United States Patent [19]
Raylman et al.

[11] Patent Number: 5,961,457
[45] Date of Patent: Oct. 5, 1999

[54] METHOD AND APPARATUS FOR RADIOPHARMACEUTICAL-GUIDED BIOPSY

[75] Inventors: Raymond R. Raylman, Morgantown, W. Va.; Richard L. Wahl, Ann Arbor, Mich.

[73] Assignee: The Regents of the University of Michigan, Ann Arbor, Mich.

[21] Appl. No.: 08/642,840

[22] Filed: May 3, 1996

[51] Int. Cl.[6] ...................................................... A61B 6/00
[52] U.S. Cl. .................... 600/436; 382/128; 250/363.02; 600/431
[58] Field of Search ................................ 128/653.1, 659, 128/654, 920, 922; 378/4, 901; 250/363.02; 382/128; 600/407, 436, 431

[56] References Cited

U.S. PATENT DOCUMENTS

| | | | |
|---|---|---|---|
| 4,259,578 | 3/1981 | Thompson | 250/363 S |
| 4,284,890 | 8/1981 | Thompson | 250/363 S |
| 4,291,228 | 9/1981 | Thompson | 250/363 S |
| 4,497,024 | 1/1985 | Roth | 364/414 |
| 5,122,667 | 6/1992 | Thompson | 250/363.03 |
| 5,230,338 | 7/1993 | Allen et al. | 128/653 |
| 5,323,006 | 6/1994 | Thompson et al. | 250/363.02 |
| 5,423,316 | 6/1995 | Hawman et al. | 128/653.1 |
| 5,483,657 | 1/1996 | Swerdloff | 378/4 |

OTHER PUBLICATIONS

Hermann et al., "Nonpalpable Breast Lesions: Accuracy of Prebiopsy Mammographic Diagnosis," *Radiology* 165:323–26 (1987).

Wahl et al., "Primary and Metastatic Breast Carcinoma: Initial Clinical Evaluation with PET with the Radiolabeled Glucose Analogue 2–[F–18]–Fluoro–2–deoxy–D–glucose," *Radiology* 179:765–770 (1991).

Khalkhali et al., "Review Of Imaging Technique For The Diagnosis Of Breast Cancer: A New Role Of Prone Scintimammography Using Technetium–99m Sestamibi," *Eur. J. Nuc. Med.* 21:357–362 (1994).

Saw et al., "Coordinate Transformations And Calculation Of The Angular And Depth Parameters For A Stereotactic System," *Med. Phys.* 14:1042–44 (1994).

Wahl et al., "Detection Of Breast Cancer In Women After Augmentation Mammoplasty Using Fluorine–18– Fluorodeoxyglucose–PET," *J. Nucl. Med.* 35:872–75 (1994).

Levivier et al., "Positron Emission Tomography–Guided Stereotactic Brain Biopsy," *Neurosurgery* 31(4):792–97 (1992).

Pirotte et al., "Use of Positron Emission Tomography (PET) in Stereotactic Conditions for Brain Biopsy," *Acta Neurochir* (Wein) 134:79–82 (1995).

Hanson et al., "FDG–PET in the Selection of Brain Lesions for Biopsy," *J. Comput. Assist. Tomogr.* 15(5):769–801 (1991).

Thompson et al., "Feasibility Study for Positron Emission Mammography," *Med. Physics* 21(4):529–38 (1994).

Mena et al., "Design and Assessment of Scintigraphy Guided Stereotaxic Localization Technique of Breast Tumors: A Phantom Study," *J. Nuc. Med.* 35:62P (1994).

Alexander et al., "Thallium–201 / Technetium–99m HMPAO single–photon emission computed tomography (SPECT) imaging for guiding stereotactic craniostomes in heavily irradiated malignant glioma patients," *Acta Neurochir* (Wein) 122:215–17 (1993).

Heywang–Kobrunner et al., "Prototype Breast Coil for MR–Guided Needle Localization," *J. Comp. Asst. Tomography* 18(6):867–81 (1994).

(List continued on next page.)

*Primary Examiner*—Marvin M. Lateef
*Assistant Examiner*—Eleni Mantis Mercader
*Attorney, Agent, or Firm*—Medlen & Carroll, LLP

[57] ABSTRACT

A medical method and apparatus for the localization and biospy of lesions in a patient body part. A radiopharmaceutical is administered to the patient followed by placement of the body part within a scanner for obtaining emission data. The emission data is converted into Cartesian coordinates which are used to guide a sampling instrument for the biopsy of said lesion.

21 Claims, 7 Drawing Sheets

OTHER PUBLICATIONS

Wanebo et al., "Fine Needle Aspiration Cytology in Lieu of Open Biopsy in Management of Primary Breast Cancer," *Ann. Surg.* 199(5):569–79 (1984).

Fischer Imaging Corporation Brochure for the Mammotest™.

Dowlatshahi et al., "Nonpalpable Breast Tumors: Diagnosis with Stereotaxic Localization and Fine–Needle Aspiration," *Radiology* 170:427–33 (1989).

Peart, "Stereostatic Localization Pinpoints Breast Lesions," *Radiologic Tech.* 62(4):234–38 (1992).

Parker et al., "Stereotactic Breast Biopsy with a Biopsy Gun," *Radiology* 176:741–47 (1990).

Parker et al., "US–guided Automated Large–Core Breast Biopsy," *Radiography* 187:507–111 (1993).

Sneige et al., "Ultrasound–Guided Fine–Needle Aspirations of Nonpalpable Breast Lesions," *A.J.C.P.* 102(1):98–101 (1993).

Raylman et al., "Stereotactic Coordinates for ECT Sinograms for Radionuclide–Guided Breast Biopsy," *J. Nuc. Med.* 37:1562–67 (1996).

METHOD AND APPARATUS FOR RADIOPHARMACEUTICAL-GUIDED BIOPSY

FIELD OF THE INVENTION

The present invention relates generally to the field of medical diagnosis and therapy, and more specifically to the localization and biopsy of suspected lesions for cell sampling or removal.

BACKGROUND OF THE INVENTION

An important aspect of the diagnosis and prognosis of breast cancer and other tumor masses is the histological assessment of the lesion, a process which normally requires the removal of a tissue sample from the mass for subsequent laboratory analysis. This sample can range from a small number of the tumor cells in the mass to the excision of the entire lesion. Collection of a suitable sample is normally accomplished by way of either a surgical biopsy or a needle biopsy.

For tumorous lesions in the breast, the initial use of an excisional surgical biopsy in order to obtain a histology sample is generally a less preferable method, given the morbidity associated with surgery and anesthesia. In addition, excisional surgical biopsy results in significant physical scarring of the patient. Since the true-positive fraction for biopsies obtained as a result of a mammographic screening program is rather low (i.e., between approximately twenty and thirty percent), the risks associated with surgical biopsy are high relative to the potential benefit. G. Hermann el al., *Radiology* 165:323–26 (1987). A less invasive needle aspiration or core biopsy is often a better alternative, given the relatively low cost and the substantial reduction in morbidity when surgery and anesthesia are avoided.

In the needle aspiration or core biopsy procedure the suspected lesion is biopsied with a sampling instrument (often a needle) and tissue cells are withdrawn for histological evaluation. Proper positioning of the sampling instrument is necessary to ensure that the removed tissue will be representative of the composition of the lesion. Accordingly, a critical aspect of the biopsy procedure is the determination of the precise location of the lesion, so that the needle can be properly positioned. In some cases, the mass is located very close to the surface of the body and the needle can be directed by palpation. In most cases, however, the lesion is located deeper in the breast and therefore palpation is not an effective way to place the biopsy needle. This same positioning problem also occurs with the localization and biopsy of non-malignant lesions, such as suspected infection or abcess.

Various methods have been developed in an attempt to localize a lesion for accurate positioning of the needle where palpation is inappropriate. One method currently in use for breast cancer patients utilizes two x-ray (mammogram) views of a compressed breast to obtain the Cartesian coordinates of the lesion. Then, under computer control, a biopsy needle is inserted and tumor material withdrawn. However, in patients with breasts which are radiographically dense, or where other anatomical organs obstruct the view of the suspected lesion, the use of this technique is limited due to poor image quality. Indeed, 20% or more of breast cancers are not seen with this approach. Ultrasound is also currently used to locate the breast mass for positioning of the biopsy needle. This technique, however, has difficulty in locating tumors which are predominantly calcifications, and in separating benign from malignant tumors.

Accordingly, there is a significant need in the art for a technique and apparatus which can precisely localize a lesion and secure the accurate placement of needle or core biopsy equipment within the lesion. Ideally, the method would allow the precise localization of any lesion in any body part, including highly calcified lesions and lesions obstructed by other anatomical organs.

SUMMARY OF THE INVENTION

The present invention contemplates a method for the localization and biopsy of lesions, comprising the steps of: a) providing i) a patient having a body part with a suspected lesion, ii) a radiopharmaceutical, iii) means for obtaining emission data from said body part of said patient; b) administering said radiopharmaceutical to said patient; c) placing said body part within said means for obtaining emission data, to detect a radiation signal created by the accumulation of said radiopharmaceutical in said lesion; d) converting said emission data into Cartesian coordinates of said lesion; and e) guiding a means for biopsying said lesion using said Cartesian coordinates. In a preferred embodiment, the lesion is a tumor lesion.

In one preferred embodiment of the method of the present invention, the radiopharmaceutical comprises a single photon-emitting radiopharmaceutical. In an alternative embodiment, the radiopharmaceutical comprises a positron-emitting radiopharmaceutical.

In another preferred embodiment of the method of the present invention, the means for obtaining emission data comprises a PET scanner. In an alternative embodiment, the means for obtaining emission data comprises a SPECT scanner. In a further alternative embodiment, the means for obtaining emission data comprises a gamma camera. In a still further embodiment, the means for obtaining emission data comprises a planar imager.

In another preferred embodiment of the method of the present invention, the means for biopsying comprises a fine needle aspiration. In an alternative embodiment, the means for biopsying comprises a core biopsy.

In another preferred embodiment of the method of the present invention, the step of converting the emission data to Cartesian coordinates further comprises the steps of: a) providing i) a display means, and ii) a user input means; b) choosing at least a first and a second view angle with said user input means; c) extracting at least one projection based on said first and second view angles; d) displaying an image of said lesion on said display means based on said projection; e) prompting a user to identify via said input means a point within said lesion; f) calculating a center of said identified lesion; g) calculating sinogram space coordinates of said identified lesion based on said first and second view angles; h) calculating cylindrical coordinates of said lesion from said sinogram space coordinates; and i) calculating said Cartesian coordinates from said cylindrical coordinates.

The present invention also contemplates an apparatus for the localization and biopsying of a lesion in a body part, comprising: a) means for obtaining emission data from said lesion; b) means for converting said emission data to Cartesian coordinates of said lesion; and c) means for biopsying said lesion located at said Cartesian coordinates. In one embodiment of the present invention, said lesion is a tumor lesion. In a preferred embodiment, the apparatus of the present invention further comprises a means for immobilizing said body part.

In one preferred embodiment of the apparatus of the present invention, the radiopharmaceutical comprises a single photon-emitting radiopharmaceutical. In an alternative embodiment, the radiopharmaceutical comprises a positron-emitting radiopharmaceutical.

In another preferred embodiment of the apparatus of the present invention, the means for obtaining emission data comprises a PET scanner. In an alternative embodiment, the means for obtaining emission data comprises a SPECT scanner. In a further alternative embodiment, the means for obtaining emission data comprises a gamma camera. In a still further embodiment, the means for obtaining emission data comprises a planar imager.

In another preferred embodiment of the apparatus of the present invention, the means for biopsying comprises a fine needle aspiration. In an alternative embodiment, the means for biopsying comprises a core biopsy.

GENERAL DESCRIPTION OF THE INVENTION

Figure 1:
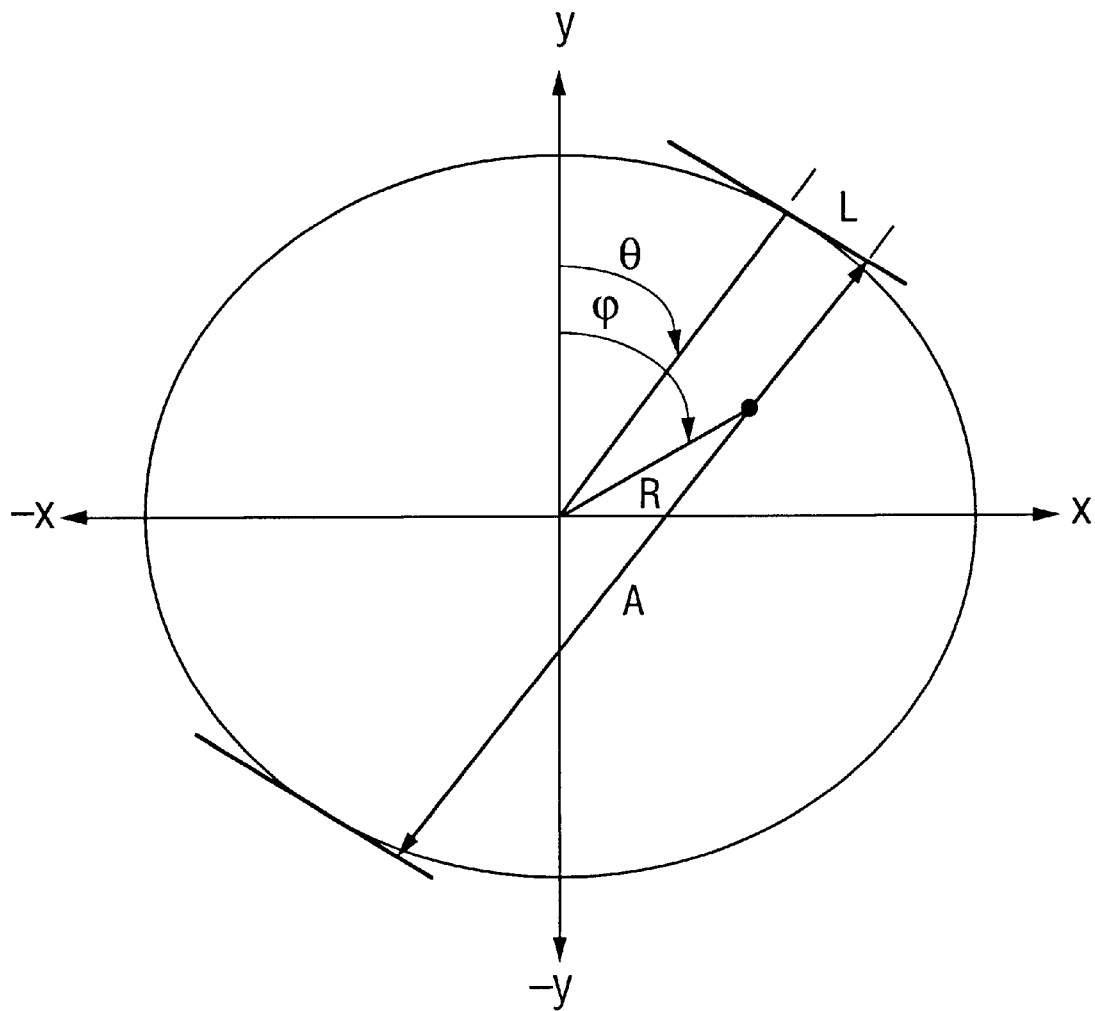
FIG. 1 provides a schematic diagram of the transformation from "scanner space" into "sinogram space" in a PET scanner.

Recently, the use of radio-tracers to detect cancer has met with considerable interest and success. The present inventors and others have shown that $^{18}$F-labeled Fluoro-deoxyglucose ("FDG") positron emission tomography ("PET") is very sensitive for detecting many breast cancers. See R. L. Wahl et al., Primary and Metastatic Breast Carcinoma: Initial Clinical Evaluation with PET with the Radiolabeled Glucose Analogue 2-[F-18]-Fluoro-2-deoxy-D-glucose, *Radiology* 179:765–770 (1991). A Fluorine-18 nucleus decays by emitting a positron which is quickly annihilated by colliding with an electron. The result of this annihilation is the production of two 511 keV gamma rays that are approximately 180 degrees apart in direction. For the PET imaging procedure, the patient receives an intravenous dose of FDG, which is preferentially accumulated in the tumor. The patient is subsequently examined with detectors that sense the resulting gamma rays.

In addition, other investigators have reported the advantageous use of single photon-emitting ("SPECT") radiopharmaceuticals such as $^{99m}$Technetium (Tc)-labeled Sestamibi and $^{201}$Thallium (Tl). These materials have also demonstrated an improved specificity and sensitivity in the detection and evaluation of breast tumors, in comparison with standard mammography techniques. See Khalkhali et al., Review Of Imaging Technique For The Diagnosis Of Breast Cancer: A New Role Of Prone Scintimammography Using Technetium-99m Sestamibi, *Eur. J. Nuc. Med.* 21:357–362 (1994). To accommodate such radiotracers, a collimator is conventionally placed in front of the detector arrays in order to define distinct line integrals (lines-of-response). Both the SPECT and PET radiopharmaceutical imaging methods are sensitive to the presence of metabolically active lesions, and are therefore able to increase the detectability of malignant tumors otherwise invisible to mammography.

The data obtained from a tomographic imaging scanner is generally organized and stored in the form of a sinogram. Sinograms obtained during standard PET and SPECT data acquisitions contain abundant information about the location of areas of increased tracer uptake (areas of tracer accumulation) The present invention therefore contemplates the application of PET- and SPECT-sinogram-derived stereotactic coordinates for the guidance of breast lesion and other tumor biopsies. In both applications, the distance from a single fiducial marker can be rapidly determined using the methods of the present invention, in contrast to other stereotactic methods, such as the Brown-Roberts-Wells technique, which require numerous fiducial points and image reconstruction. See Saw C. B., et al., Coordinate Transformations And Calculation Of The Angular And Depth Parameters For A Stereotactic System, *Med. Phys.* 14:1042–44 (1994). In addition, using the methods of the present invention transmission scans to provide attenuation correction maps are unnecessary in most cases. Since image reconstruction and attenuation correction are not required, the method of the present invention considerably simplifies the spatial localization of tracer uptake detected with PET and SPECT systems.

It is significant to note that only two views are actually required to calculate the lesion position using the methods of the present invention, although more can be utilized. Thus, the methods and apparatus of the present invention can also be advantageously applied using planar emission data, such as that provided by a planar imager with a single array of detectors, or alternatively a single-headed gamma camera. Indeed, it is contemplated that the use of a planar imager or gamma camera may in fact serve to increase the efficiency of the method and apparatus of the present invention, since only the necessary views need be acquired, and the detectors can be placed very close to the body part of interest, such as the breast.

DEFINITIONS

In considering the present radiopharmaceutical-guided biopsy invention, some definitions are helpful. For example, "display means" refers to any type of monitor such as a computer monitor or television. A "user input means" refers to any device useful for allowing a user to input information into the processor which executes the software of the present invention. For example, a keyboard, a mouse, a computer graphic pencil, etc.

"Sinogram space coordinates" refers to the coordinates in the sinogram reference frame. These coordinates typically comprise L, which refers to the distance from the center of the detector array to the line integral of photons detected from the object, and θ which refers to the angular position of the detector array. "Cylindrical coordinates" refers to the coordinates in the scanner reference frame, or in the "scanner space." These coordinates typically comprise R, which is the distance from the object (i.e. lesion) to the center of the scanner, and φ, which is the angular position of the object (i.e. lesion) relative to the center of the scanner. "Cartesian coordinates" refers to the x-, y-, and z-coordinate system.

"PET" refers to positron emission tomography, while "SPECT" refers to single photon emission computed tomography.

DETAILED DESCRIPTION OF THE PREFERRED EMBODIMENTS

The following description serves to illustrate a preferred embodiment and aspects of the present invention and is not to be construed as limiting the scope thereof.

More specifically, the present invention provides methods and an apparatus which utilizes emission data contained in conventional sinograms to rapidly determine the three-dimensional position (utilizing the Cartesian coordinate system) of any radiopharmaceutical-avid site in the field-of-view of an emission scanner, without image reconstruction or co-registration with an anatomical image.

An object imaged in a typical sinogram can be characterized by its radius (R), angular position ($\phi$) and axial position. The radius is the distance from the object to the center of the scanner. The angular position of the object is defined relative to the twelve o'clock position of the scanner, while the axial position is defined relative to the top edge of the scanner. The cylindrical coordinates are transformed, by the scanning process, to data which gives the position of the object in terms of its distance from the center of projections acquired at numerous angles relative to the scanner reference frame ("sinogram space"). Utilizing two of these views from each sinogram in a set of sinograms (one sinogram is acquired for each of the two image planes) the object's position can be transformed back into the cylindrical coordinate system of the scanner. The cylindrical coordinates of the object can then be converted into the Cartesian coordinate system, which can be utilized by the apparatus of the present invention to precisely perform a needle biopsy procedure resulting in either sampling or complete excision of the tumor mass.

I. Detection of Photon and Gamma Emissions From Radiopharmaceuticals

Emission scanners acquire line integrals, or lines-of-response integrating the radioactivity within the volume defined by the shape and position of the detectors. The line integral provides an indication of the radiopharmaceutical emissions originating from within the field-of-view. For each image plane data is stored in a two-dimensional array or sinogram; where each row denotes the view angle at which the detector array was positioned and each element within a row contains the number of events detected by an individual detector within an array of detectors.

FIG. 1 provides a schematic drawing of the geometrical relationship between an object and a detector array in a typical PET emission scanner. The line integral or line-of-response under consideration is designated as "A" in FIG. 1. The scanning process transforms the position of a photon- or positron-emitting object from cylindrical coordinates (R and $\phi$) into the "sinogram space" coordinates L and $\theta$. This transformation can be expressed by the equation:

$$L = R \cdot \sin(\phi - \theta). \tag{1}$$

The parameter L is the distance from the center of the detector array to the line integral of photons or gamma rays detected from the object; $\theta$ is the angular position of the detector array.

II. Calculation Of Three-Dimensional Cartesian Coordinates

Given a set of sinograms and Equation (1) it is possible to calculate the position of an object in the scanner coordinate reference frame. This calculation requires data from two views. By selecting data acquired at view angles of $\theta=0°$ and $\gamma$ from a sinogram we can re-write Equation (1):

$$L_1 = R \cdot \sin\phi; \ [\theta=0°] \text{ and} \tag{2}$$

$$L_2 = R \cdot \sin(\phi-\gamma) = R \cdot [(\sin\phi \cdot \cos\gamma) - (\cos\phi \cdot \sin\gamma)]; \ [\theta=\gamma]. \tag{3}$$

Where, $L_1$ is the distance from the line integral sampling the photon flux from the object to the center of the detector array positioned at a rotation angle $\theta=0°$. $L_2$ is the distance from the line integral to the center of the detector array at a rotation angle $\theta=\gamma$. Equation (3) was cast into a more useful form by insertion of the trigonometric identity for $\sin(\phi-\gamma)$. Dividing Equation (3) by (2) we obtain:

$$\frac{L_2}{L_1} = \cos\gamma - \cot\phi \cdot \sin\gamma. \tag{4}$$

Since the distances $L_1$ and $L_2$ can be obtained from the sinograms and $\gamma$ is given, Equation (4) can be solved for the angular position of the object in the scanner ($\phi$). The object's distance from the center of the scanner (R) can then be calculated from Equation (2). The x and y- coordinates of the object in the scanner reference frame are given by $x=R \cdot \sin\phi$ and $y=R \cdot \cos\phi$. The z-coordinate is determined by first locating the detector plane which sampled the center of the object and then, given the spacing between planes, calculating the axial distance from the top plane of the scanner to the object.

Photons or gamma rays reaching two detector arrays at different rotation angles can pass through greatly different amounts and types of attenuating material; such as that encountered in the upper torso. Since the application of attenuation correction is preferably avoided to minimize acquisition and processing time, there can be substantially unequal image intensities between the two views. This problem is reduced in a preferred embodiment of the present method problem by selecting two view angles that are symmetric about the y-axis ($\pm\gamma$). Thus, the type and total amounts of tissue traversed by the photons is more balanced for the two sets of data, thereby facilitating the localization of the centroid of the object in both views.

When symmetric view angles are employed, the original x-y coordinate axis is rotated by the angle $-\gamma$ to a new coordinate system x'-y'. In this system $L_1$ and $L_2$ retain their previous definitions, while the total view angle ($\gamma$) becomes $2\gamma$.

Therefore, Equation (2) remains the same and Equation (4) becomes:

$$\frac{L_2}{L_1} = \cos 2\gamma - \cot\phi' \cdot \sin 2\gamma. \tag{5}$$

From Equation (5) and Equation (2), the position of the object in the rotated reference frame (R' and $\phi'$) is determined, allowing calculation of x' and y'. The z-coordinate is calculated as previously described. A transformation back to the un-rotated scanner coordinates is applied to obtain the position of the object in the scanner.

III. Means for Converting the Emission Data to Cartesian Coordinates

FIG. 2 illustrates a flowchart of one embodiment of the software utilized in the present invention to convert radiopharmaceutical emission data to Cartesian coordinates. This preferred embodiment was used in the experiments described more fully below. Although any suitable programming language can be used to implement the flowchart, in the preferred embodiment, the software is written in IDL (Interactive Data Language; RSI, Boulder Colo.). Furthermore, it should be apparent to one skilled in the art that the flowchart is not solely limited to implementation by a processor executing software, but could also be implemented with hardware components only, or alternatively by a combination of hardware and software.

Figure 2A:
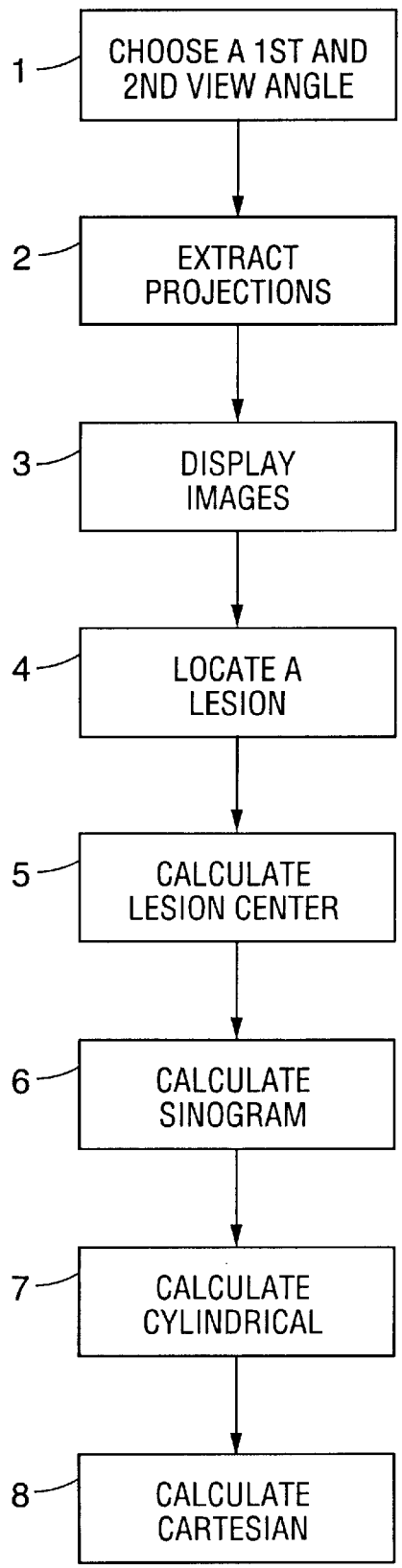
FIG. 2a is a basic flowchart of a preferred embodiment of the software utilized in the present invention to convert the emission data to Cartesian coordinates.

The basic flowchart illustrated in FIG. 2a begins at block 1 by choosing a first and second view angle for examining the lesion. A projection is then extracted from each view angle in block 2. An image of each projection is then displayed for a user at block 3. Block 4 then prompts a user to locate a lesion in the displayed image. The center of the lesion is then calculated at block 5. Blocks 6–8 then calculates the different coordinate systems from the sinogram coordinate system to the cylindrical coordinate system until finally, the Cartesian coordinate system is calculated.

Figure 2B:
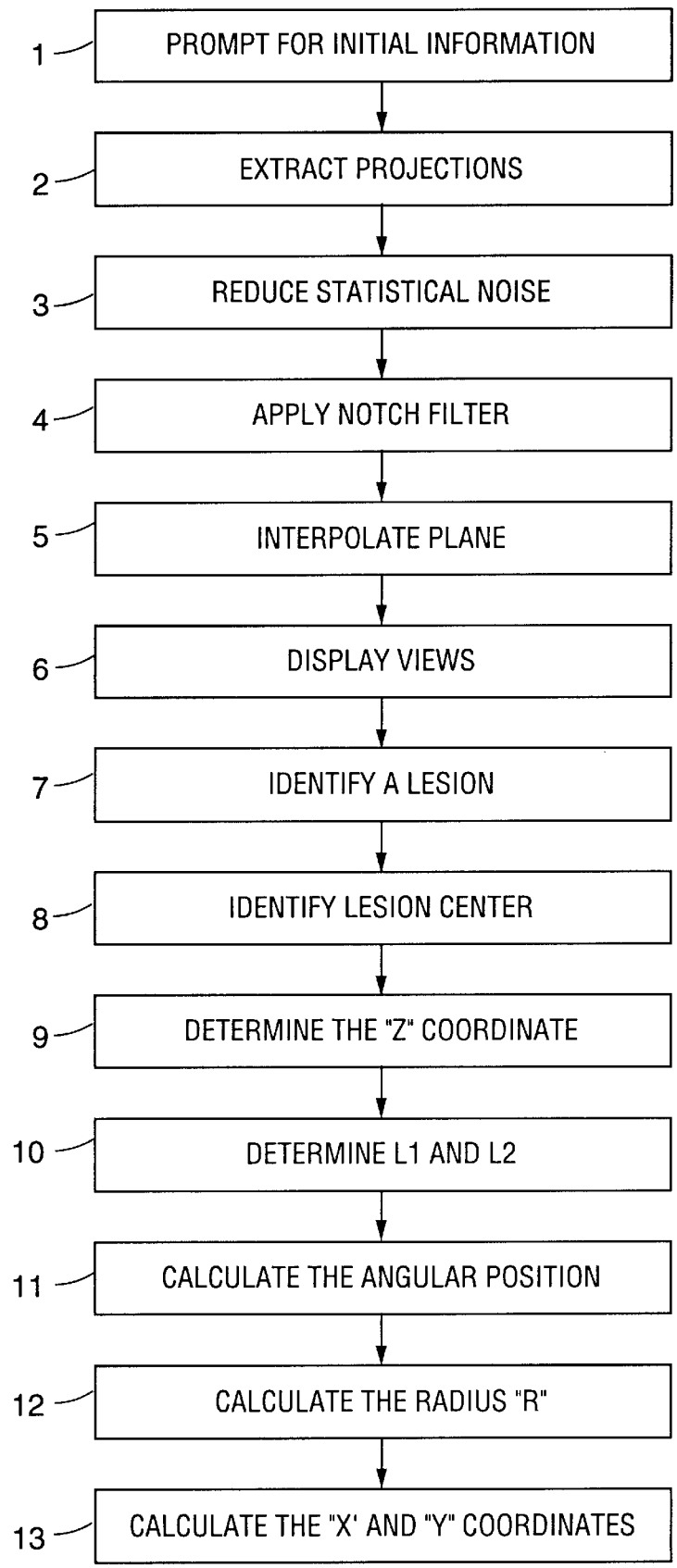
FIG. 2b is a more detailed flowchart of a particularly preferred embodiment of the software utilized in the present invention to convert the emission data to Cartesian coordinates.

The flowchart illustrated in FIG. 2b illustrates a more detailed flowchart, which begins at block 1 by prompting a user for specific initial information. The user enters the sinogram file name for holding the emission data; the normalization file name (in the case of PET scans) which provides for the normalization of the individual detector efficiencies in the scanner; and a first and second view angle. While any number of a plurality of view angles maybe examined, in the preferred embodiment the present invention utilizies only two view angles. In a particularly preferred embodiment, the two view angles are selected so as to be symmmetric about the y-axis ($\pm\gamma$).

In one embodiment of the present invention, the means for obtaining emission data included a commercially-available Siemens ECAT 931 PET scanner (Hoffman Estates, Ill.). In an alternative embodiment of the present invention, the means for obtaining emission data included a commercially-available Picker Prism XP3000 SPECT scanner (Solon, Ohio). At block 2, the appropriate projections from 15 sinograms for the specified first and second view angles acquired on either the Siemens ECAT 931 or the Picker Prism 3000XP are extracted. These projections are determined by the first and second view angles, taking into account the angular sampling frequency of the emission scanner.

At block 3, the effects of statistical noise resulting from background radiation are reduced by summing 5 projections for the first and second view angles. At block 4, a suitable filter is applied to the summed projections in order to enhance tumor contrast. In a preferred embodiment, this filter comprises a notch filters, which operates to filter both low and high frequencies from a signal.

Since the spacing between lines-of-response for a Siemens ECAT 931 is 3.13 mm and the spacing between image planes is 6.74 mm, data from adjacent image planes are interpolated at block 5 to obtain equivalent ray spacing in all directions. A linear interpolation algorithm is then used to create a new data set which expands the 15 planes to 29. Thus, each composite view is stored in a 192×29 matrix; where the transaxial pixel spacing is 3.13 mm and axial spacing is 3.37 mm. The axial spacing denotes the spacing of the detectors along the axis of the scanner, while transaxial spacing denotes the separation between discrete detectors in the detector arrays. In an alternative approach two sets of sinograms acquired with a 3.37 mm axial separation are interleaved; however, this increases the time required for the procedure. Data acquired with the Picker Prism XP3000 was stored in a 128×29 matrix; no interpolation was necessary because axial and transaxial pixel spacing is uniform (3.56 mm). Thus, block 5 was not followed in this particular embodiment.

It should be noted that while the steps illustrated by blocks 3–5 are provided in a particularly preferred embodiment of the present invention, they are not crucial to the operation of the present software.

The flowchart continues at block 6 by displaying two views of the lesion corresponding to the first and second view angles. At block 7, the user identifies a lesion. In a preferred embodiment this can be performed by using a mouse and pointer to click to the lesion on the display. The center of the lesion can be located in both views at block 8. By locating the center of the lesion, the Cartesian coordinate Z can easily be determined at block 9. As discussed earlier, Z can be determined by calculating the axial distance from the top plane of the scanner to the lesion.

At block 10, the parameter $L_1$ corresponding to the distance from the line integral sampling the photon flux from the lesion to the center of the detector array positioned at the first view angle and $L_2$ corresponding to the distance from the line integral sampling the photon flux from the lesion to the center of the detector array positioned at the second view angle are then determined. Because $L_1$, $L_2$, the first view angle and the second view angle are known, equation 4, shown above, can be utilized at block 11 to calculate the angular position ($\phi$). From there, the radius R is calculated at block 12. Finally, the Cartesian coordinates x and y can be obtained at block 13 by utilizing the formulas $x=R\cdot\sin\phi$ and $y=R\cdot\cos\phi$.

IV. The Radiopharmaceutical-Guided Biopsy Apparatus

The apparatus of the present invention preferably comprises a means for obtaining emission data from a body part, such as a PET or SPECT scanner, coupled with a means for converting the emission data into Cartesian coordinates and a means for aspirating a tumor lesion located within the body part. In a particularly preferred embodiment, the apparatus further comprises a means for immobilizing said body part.

In one preferred embodiment, the body part is infiltrated with a suitable positron-emitting radiopharmaceutical, such as 2-[F-18]-fluoro-2-deoxy-D-glucose (FDG), which is preferentially accumulated within the tumor lesion. In this embodiment, the radiotracer produces gamma rays and the means for obtaining emission data includes one or more detector modules each of which has at least one sensor array of gamma ray-sensitive material (scintillator), such as bismuth germanate crystals, mounted on a position detector such as a photomultiplier array or position sensitive photomultiplier.

Alternatively, individual light sensors, such as avalanche photodiodes can be mounted upon each gamma ray detector in the array. In a still further embodiment, each detector module has a continuous sheet of gamma ray detecting material which is mounted upon a position sensitive multiplier or photomultiplier array. The continuous sheet of gamma ray sensitive material can have slots with septa on its surface, which would operate in a manner similar to the block detectors known in the art of PET scanners. Preferably, each detector module also has dense shielding for reducing undesirable emissions from other parts of the body.

In an alternative embodiment, the radiopharmaceutical comprises a suitable single photon-emitting radiotracer, such as Technetium-99m Sestamibi. In this embodiment of the invention, a conventional collimator is positioned between the object and one or more of the detector modules, and the apparatus is operated in a non-coincident mode. While excellent results can be obtained from data acquired in measurements utilizing the single photon-emitting radionuclide $^{99m}$Tc, the higher absorption of the relatively low energy photons emitted by many single photon-emitting radiopharmaceuticals will require special considerations (e.g., $^{201}$Tl).

For instance, in applications with $^{201}$Tl where the tumors are deep inside the body, it may be necessary to employ attenuation corrections. In the case of breast biopsies, however, the increased attenuation is, to a certain extent, advantageous. The flux of background gamma rays emanating from the myocardium and other relatively deep structures is reduced by attenuation. While attenuation will also reduce the gamma ray flux from tumors, axial compression of the breast lessens this effect by reducing the amount of tissue traversed by transaxially directed gamma rays before exiting the breast.

It is contemplated that the means for immobilizing the body part can include a table and a compression arm which compresses the body part against the table. The table may further include a suitable aperture, as is present in many conventional scanning systems. In an alternative and preferred embodiment, the means for immobilizing the body part comprises an opposing pair of compression paddles, with the body part placed therebetween. These compression paddles can be advantageously constructed of any suitable material, such as Lucite™, and in a particularly preferred embodiment a grid of small needle guide holes are provided through one of the compression paddles, to assist the technician or physician in localizing and inserting the needle for the biopsy procedure.

It is also contemplated that any number of fiducial markers can be incorporated into the apparatus of the present invention. However, as discussed above, only a single fiducial marker containing a suitable radioactive substance is actually required for use in the methods of the present invention. Accordingly, in a preferred embodiment only one fiducial marker is included in the apparatus of the present invention. This marker can be constructed of any suitable material, such as a block of plastic or Lucite, to form a spherical cavity with radioactivity.

Since the method of the present invention can be utilized with both sinogram and planar emission data, the means for obtaining emission data can comprise either a conventional PET or SPECT detector, or alternatively a single planar imager or single headed gamma camera (including cameras fitted with 511 keV collimators). In the foregoing embodiments the means for converting said emission data to Cartesian coordinates preferably comprises a separate modular device which can be easily affixed to the PET, SPECT or gamma camera bed. This allows conventional scanning and detection devices to be temporarily converted to a radiopharmaceutical-guided biopsy apparatus as contemplated by the present invention.

It is further contemplated that the means for obtaining the emission data and for converting that data into Cartesian coordinates can be advantageously combined with the means for aspirating the tumor lesion, into a dedicated radiopharmaceutical-guided biopsy apparatus possessing a small number of high resolution detectors. This embodiment is easily constructed at a relatively small fraction of the cost of a PET or SPECT system. For example, the positron emission mammography device described in U.S. Pat. No. 5,323,006 to Thompson el al., hereby incorporated by reference, could be used in conjunction with the method of the present invention, to guide core biopsies of breast masses.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); kg (kilograms); $\mu$g (micrograms); L (liters); ml (milliliters); $\mu$l (microliters); cm (centimeters); mm (millimeters); $\mu$m (micrometers); nm (nanometers); °C. (degrees Centigrade); sec (seconds); msec (milliseconds); kBq (kiloBecquerells); mBq (milliBecquerells); STD (standard deviation); SUV (standard uptake values); keV (kiloelectronvolt)

EXAMPLE 1

Localization of Lesions in Phantom Breast Using PET Scanning

Four hollow spheres (diameters ranging from 1.6 to 3.4 cm) containing $^{18}$F (concentration=222 kBq/ml) were positioned at unique locations inside a large elliptical tank (the phantom) filled with water. The phantom was then carefully positioned in a Siemens ECAT 931 PET scanner and a 15 minute static PET acquisition was performed. No attenuation or scatter corrections were applied.

Figure 4:
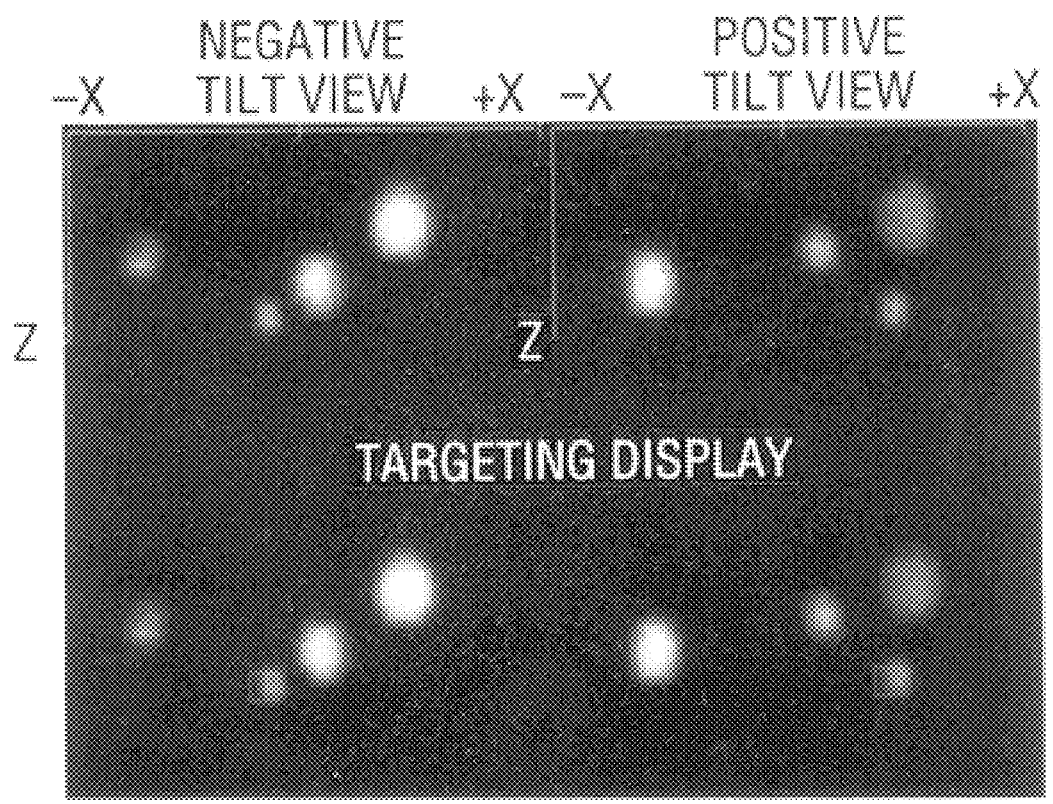
FIG. 4 illustrates a user display from the stereotactic software showing an image of four spheres filled with $^{18}$F in an elliptical tank.

FIG. 4 shows the display produced on the display means, using the preferred embodiment of the software described above. To convert the emission data from the scanner into Cartesian coordinates, the user was prompted to select the center of the object (in both views) whose position must be calculated. The software then used data from within a 6×6 pixel search area surrounding this point to calculate the center of a mass of radiation counts within this region. The coordinates of the object were then calculated and displayed. FIG. 4 also illustrates the relatively uniform image intensities of the spheres in the two views, although the effects of increased attenuation of the deepest objects is apparent.

Figure 5A:
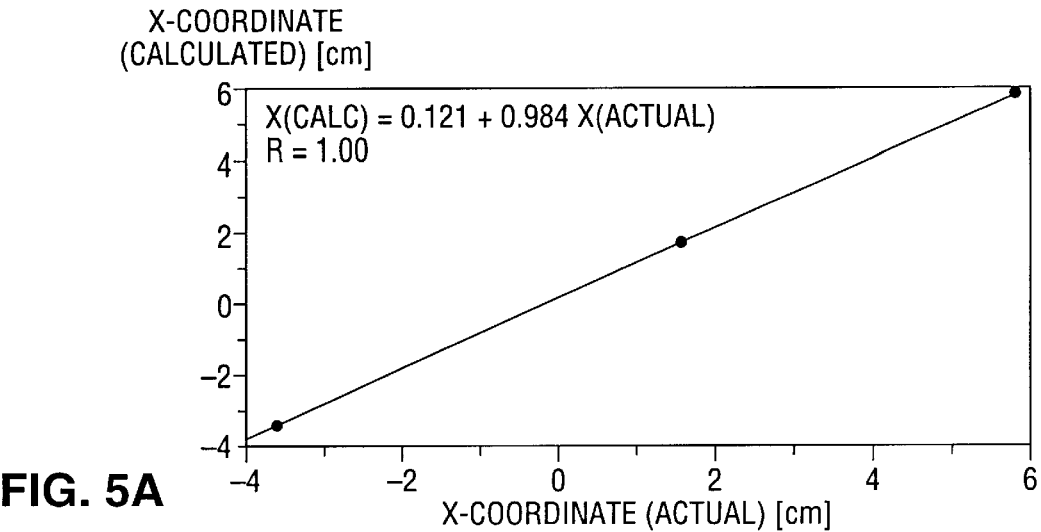
FIGS. 5a, 5b and 5c provide graphs comparing the calculated (mean±STD) versus known positions of spheres filled with $^{18}$F for the x-, y- and z-coordinates, respectively.
Figure 5B:
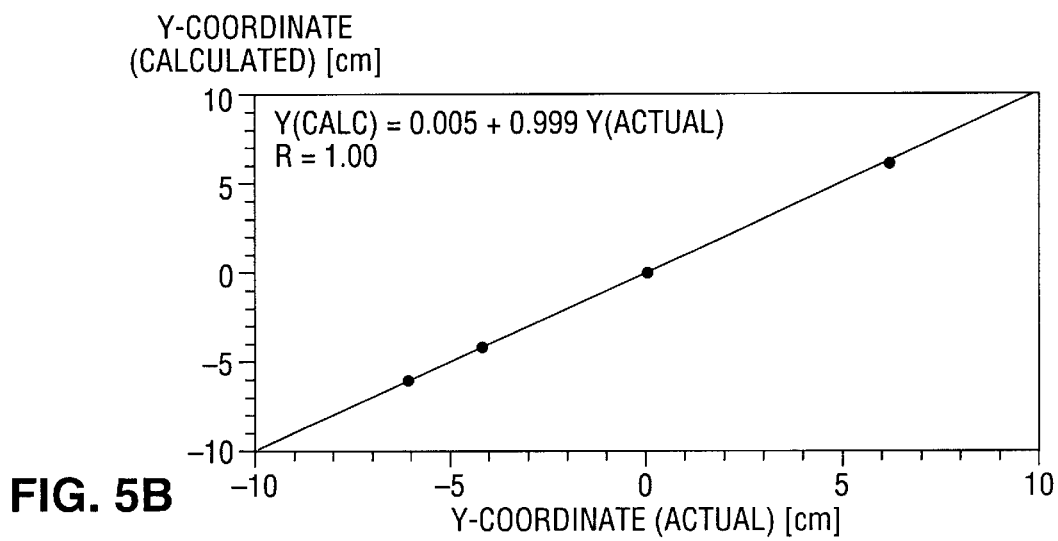
Figure 5C:
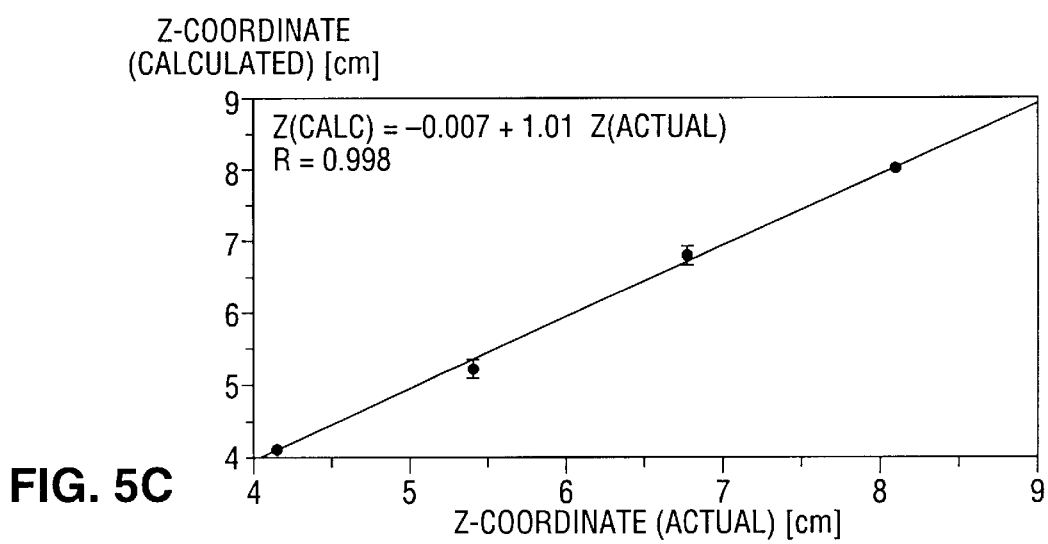

Data from five independent measurements were used to calculate the mean position of the spheres. These results were then compared to the known locations. The results from this validation experiment are shown in the plots of FIG. 5. There was excellent correlation between the calculated and actual values. Lines fit to the data have slopes ranging from 0.984 to 1.01 and R-values ranging from 0.998 to 1.0. The largest y-axis-intercept was 1.21 mm, calculated for the x-coordinate. Data for the x-coordinate also produced the slope with the largest deviation from unity (0.984). These small errors were most probably due to a minor error in positioning of the phantom in the scanner. The greatest standard deviation calculated for the coordinates of the spheres was 3.3 mm. The plot displaying the x-coordinate data appears to have only 3 points. Actually, two spheres had identical x-coordinates (−4.3 cm) and their data points are plotted very close together. The results shown in FIG. 5 demonstrate the high degree of accuracy in locating the position of photon-emitting objects attainable with this method.

EXAMPLE 2

Localization of Lesions in Phantom Breast Using SPECT Scanning

The same phantom was used to test the ability of this method to locate areas of increased single photon-emitting (SPECT) radiopharmaceutical uptake. The four spheres were filled with $^{99m}$Tc (222 kBq/ml). Data was acquired using a Picker Prism 3000XP triple head SPECT scanner. A 360° step and shoot acquisition was performed (30 seconds per stop, each head moved 120°), each view was acquired at 1° increments. Although a plurality of views were acquired, only two views were analyzed. Following the data acquisition, two sinograms were utilized to calculate the Cartesian coordinates of each sphere, as described in Example 1. Data from five independent measurements were used to calculate the mean position of the spheres. These results were then compared to the known locations. Similar results were obtained from data acquired with a Picker Prism 3000XP SPECT scanner with the spheres filled with $^{99m}$Tc.

EXAMPLE 3

Removal of lesions Using Emission-Guided Needle Biopsy Apparatus

Figure 3:
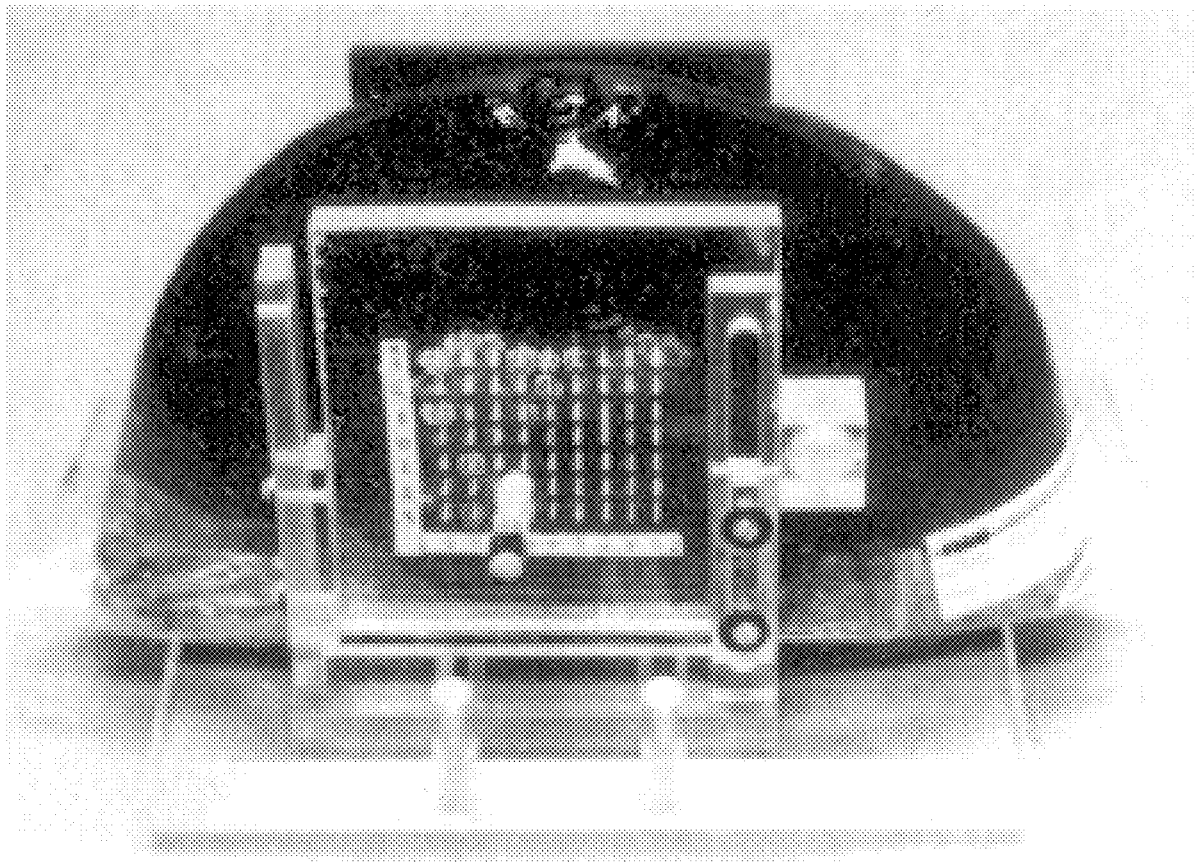
FIG. 3 illustrates one preferred embodiment of the means for immobilizing the body part as contemplated for use in the present invention.

One embodiment of the method and apparatus of the present invention was then used to facilitate the biopsies of $^{18}$F-FDG- or $^{99m}$Tc-Sestamibi-avid lesions. A compressed breast with lesions was simulated using a specially manufactured phantom (Gammex/RMI; Madison Wis.). This phantom contains hollow regions which can be filled with radiopharmaceuticals. FIG. 3 illustrates this phantom placed between the compression paddles described above. The lesions are approximately 1 cm in diameter and in this example contained FDG concentrations equivalent to standard uptake values ("SUV") ranging from 1 to 7 (assuming a 370 mBq injection of FDG and a 70 Kg patient). These values span the lower range of SUV values reported for FDG in human breast cancer 1 hour following infusion. R. L. Wahl et al., Detection Of Breast Cancer In Women After Augmentation Mammoplasty Using Fluorine-18-Fluorodeoxyglucose-PET, *J. Nucl. Med.* 35:872–75 (1004).

The long axis of the simulated compressed breast phantom (the long axis of the compressed breast is perpendicular to the direction of compression as illustrated in FIG. 2) mounted in the biopsy device was aligned with the axis of the ECAT 931 PET scanner. A 10 minute static acquisition was performed and the sinograms used to calculate the positions of the fiducial marker and lesion. From the calculated positions of the fiducial marker and the simulated tumor, the software determined the proper needle guide hole and the necessary needle insertion depth.

In all of the simulated breast tumor biopsies (N=10) the needle successfully penetrated the sham lesions and 90% of the liquid was withdrawn from the spheres. It is important to note that all simulated biopsies were performed using coordinates calculated from the sinogram-based method, no visual guidance of the biopsy needle was utilized.

EXAMPLE 4

Localization of Breast Lesion with Background Emissions

The object of this experiment was to analyze the effect of tracer uptake in the normal breast tissue surrounding a lesion. Another phantom was constructed consisting of a 3 cm×9 cm×10 cm tank (representative of a large compressed breast) containing two hollow spheres (1.27 cm diameter) which could be filled with photon-emitting radiopharmaceuticals. In addition, a third sphere was attached to the exterior of the tank to serve as a fiducial marker. To simulate tumor contrast in a typical breast biopsy, the spheres were filled with $^{18}$F (37 kBq/ml; SUV=7 for a 370 MBq injection and a 70 Kg patient). The tank was filled with a solution containing $^{18}$F (4.63 kBq/ml; SUV=0.875 for a 370 MBq FDG injection and a 70 Kg patient). Thus, a tumor-to-background ratio of 8-to-1 was achieved; reasonably typical of FDG contrast one hour post-injection in human studies. R. L. Wahl et al., Detection Of Breast Cancer In Women After Augmentation Mammoplasty Using Fluorine-18-Fluorodeoxyglucose-PET, *J. Nucl. Med.* 35:872–75 (1004).

Again, the long axis of the phantom was coaxial with the axis of the scanner. A 15 minute data acquisition, with no attenuation correction, was performed. Positions of the two simulated lesions relative to the fiducial marker were determined and compared to the known relative tumor locations. This phantom was also filled with appropriate amounts of $^{99m}$Tc to obtain a tumor-to-background ratio of 4, which is in the upper part of the range of values reported in humans by Khalkhali et al., to test the ability to locate $^{99m}$Tc-labeled-Sestamibi-avid breast tumors.

Figure 6:
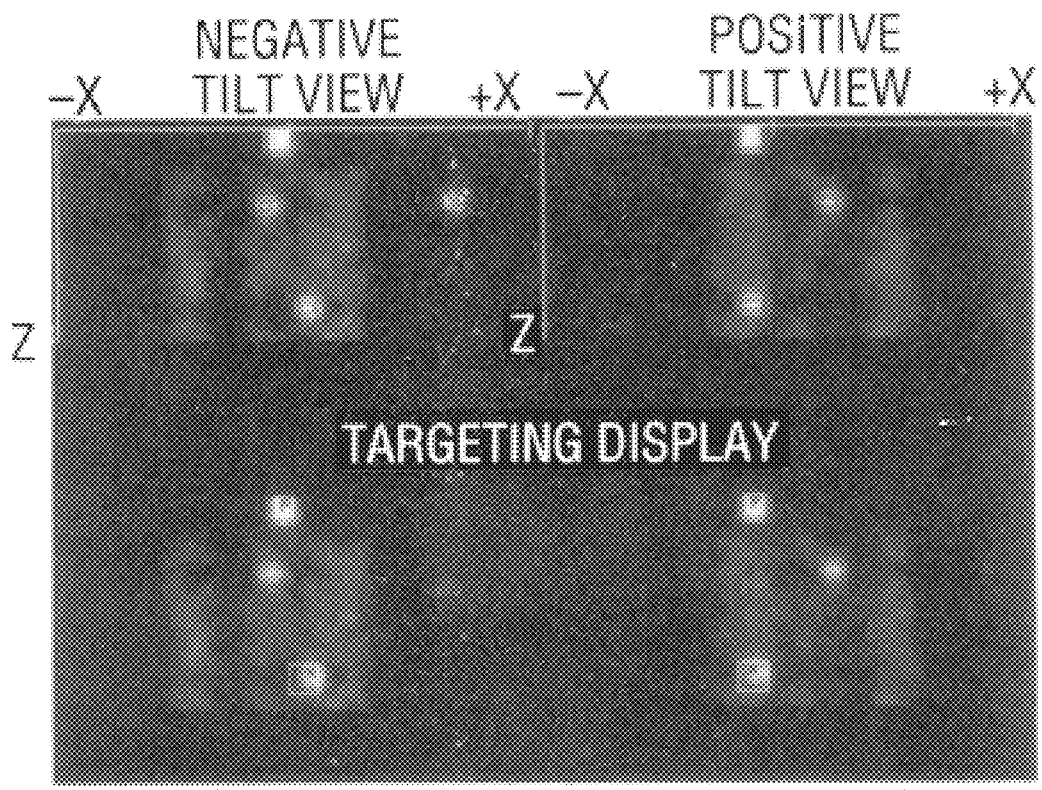
FIG. 6 provides a stereotactic image of the compressed breast phantom containing background activity.

FIG. 6 shows the images obtained of the breast phantom with simulated normal tissue background. In order to confirm the ability to biopsy these "tumors", their positions relative to the fiducial marker were calculated. Relative coordinates determined from a PET scan for sphere I are: (1.77 cm, −3.05 cm, 2.90 cm), and for sphere II: (0.61 cm, 0.90 cm, 7.64 cm). Using a SPECT camera the relative position of sphere I was calculated to be: (1.77 cm, −3.19 cm, 2.87 cm) and for sphere II: (0.79 cm, 0.77 cm, 7.54 cm).

The actual coordinates measured from the phantom for sphere I were: (1.61 cm, −3.19 cm, 2.96 cm), for sphere II: (0.65 cm, 0.82 cm, 7.75 cm). Errors present in the positions of the fiducial mark and tumors propagate to create the errors in calculations of relative position. It is apparent, however, that these errors did not significantly affect the localization of the simulated lesions. Accordingly, the application of the methods and apparatus contemplated by the present invention yielded excellent results for data obtained with both PET and SPECT scanners.

The PET-guided biopsy display, shown in FIG. 7, demonstrates that, given proper choice of view angles, the simulated tumors were clearly detectable, even in the presence of background activity. Reduction of photon attenuation effects and scatter from myocardial uptake was accomplished by choosing a large view angle. At these angles photons which reach the detector array have traversed a minimum of breast and upper torso tissue. In addition, viewed at these angles, images of the myocardium and breast areas in most patients will not overlap. Contamination of the signal from breast tumors due to myocardial activity, therefore, is minimized, which is especially important for Sestamibi- and FDG-guided biopsies. As demonstrated in these experiments, large view angles still allow accurate stereotactic calculation of the lesion positions.

Furthermore, large view angles aid in increasing the tumor-to-background contrast. This effect is related to the fact that the individual elements in a sinogram are the results of an integral along the detectors' lines-of-response. The present invention contemplates that breast compression is preferentially applied perpendicular to the long axis of the body; hence the long axis of the compressed breast is co-axial with the long axis of the body. Therefore, if the patient is placed on a standard scanning bed, the long axis of the compressed breast is aligned with the axis of the scanner. In this orientation, compression of the breast, in addition to stabilizing the breast during biopsy, reduces the effective thickness of the breast in the transaxial plane. Hence, the detector response ray-lengths through the compressed breast is lessened and are minimized at angles close to 90° (angles of 0° and 90° cannot be used in this method to calculate stereotactic coordinates).

Two effects emerge as the intersection lengths are reduced. First, for detectors sampling signal from tumor, the fractional contribution of tumor to the line integrals is increased. Second, for detectors sampling normal tissue, the amplitude of the line integral is reduced. Both effects act to increase the contrast between tumor and normal tissue by reducing the amount of background activity included in the data set. Since the present method for the determination of the object position performs relatively well at most view angles (except at angles close to 0° and 90°), the optimal view angle is the one at which the best tumor-to-background contrast occurs. This angle can vary depending upon the patient's physiology and anatomy.

From the above, it is clear that the present invention provides for a technique and apparatus which can precisely localize a tumor lesion and secure the accurate placement of needle biopsy equipment within the tumor mass. While a preferred embodiment has been described in some detail, it should be apparent from the above discussion that many modifications and variations are possible without deviating from the invention. For example, while the description of the invention and the examples provided herein involve only breast tumors, it is also contemplated that, with only slight modifications, the methods and apparatus of the present invention can be utilized to guide biopsies of tumor lesions located elsewhere in the human body. Similarly, the methods and apparatus of the present invention can also be advantageously utilized to guide biopsies of other types of lesions, such as suspected infections or inflammatory processes, or any other disease process which can be detected by the accumulation or non-accumulation of radiopharmaceuticals. In principle, alternative imaging technologies such as magnetic resonance imaging and ultrasound may also be incorporated into the methods and apparatus of the present invention, with appropriate modifications. Furthermore, other improvements and modifications which become apparent to persons of ordinary skill in the art only after reading this disclosure, the drawings and the following claims are deemed within the spirit and scope of the present invention.

We claim:

1. A method for the localization and biopsy of lesions, comprising the steps of:
   a) providing i) a patient having a body part with a suspected lesion, ii) a radiopharmaceutical, iii) means for obtaining emission data from said body part of said patient;
   b) administering said radiopharmaceutical to said patient;
   c) placing said body part within said means for obtaining emission data, to detect a radiation signal created by the accumulation of said radiopharmaceutical in said lesion;
   d) obtaining the sinogram space coordinates generated by said means for obtaining emission data for said radiation signal;
   e) converting said sinogram space coordinates into cylindrical coordinates;
   f) converting said cylindrical coordinates into Cartesian coordinates corresponding to said lesion; and
   g) guiding a means for biopsying said lesion using said Cartesian coordinates.

2. The method of claim 1, wherein said lesion is a tumor lesion.

3. The method of claim 1 wherein said radiopharmaceutical comprises a single photon-emitting radiopharmaceutical.

4. The method of claim 1 wherein said radiopharmaceutical comprises a positron-emitting radiopharmaceutical.

5. The method of claim 1 wherein said means for obtaining emission data comprises a PET scanner.

6. The method of claim 1 wherein said means for obtaining emission data comprises a SPECT scanner.

7. The method of claim 1 wherein said means for obtaining emission data comprises a gamma camera.

8. The method of claim 1 wherein said means for obtaining emission data comprises a planar imager.

9. The method of claim 1 wherein said means for biopsying comprises a fine needle aspiration.

10. The method of claim 1 wherein said means for biopsying comprises a core biopsy.

11. A method for the localization and biopsy of lesions, comprising the steps of:
   a) providing i) a patient having a body part with a suspected lesion, ii) a radiopharmaceutical, iii) means for obtaining emission data from said body part of said patient, iv) a display means, and v) a user input means;
   b) administering said radiopharmaceutical to said patient;
   c) placing said body part within said means for obtaining emission data, to detect a radiation signal created by the accumulation of said radiopharmaceutical in said lesion;
   d) choosing at least a first and a second view angle with said user input means;
   e) extracting at least one projection based on said first and second view angles;
   f) displaying an image of said lesion on said display means based on said projection;
   g) prompting a user to identify via said input means a point within said lesion;
   h) calculating a center of said identified lesion;
   i) obtaining sinogram space coordinates of said identified lesion based on said first and second view angles;
   j) converting said sinogram space coordinates into cylindrical coordinates;
   k) converting said cylindrical coordinates into Cartesian coordinates corresponding to said lesion; and
   l) guiding a means for biopsying said lesion using said Cartesian coordinates.

12. An apparatus for the localization and biopsy of a lesion in a body part, comprising:
   a) means for obtaining emission data created by the accumulation of a radiopharmaceutical in said lesion, under conditions such that scanner space coordinates are generated;
   b) converting means coupled to said means for obtaining emission data for calculating x, y and z Cartesian coordinates of said lesion from said scanner space coordinates generated by said means for obtaining emission data; and
   c) means for biopsying said lesion located at said Cartesian coordinates.

13. The apparatus of claim 12, further comprising a user input means coupled to said means for obtaining emission data for choosing at least two view angles of said body part in order to extract at least one projection of said lesion.

14. The apparatus of claim 13, wherein said user input means utilizes a first and a second view angle of said body part in order to extract at least one projection of said lesion.

15. The apparatus of claim 12, wherein said lesion is a tumor lesion.

16. The apparatus of claim 12 wherein said radiopharmaceutical comprises a single photon-emitting radiopharmaceutical.

17. The apparatus of claim 12 wherein said radiopharmaceutical comprises a positron-emitting radiopharmaceutical.

18. The apparatus of claim 12 wherein said means for obtaining emission data comprises a gamma camera.

19. The apparatus of claim 12 wherein said means for obtaining emission data comprises a planar imager.

20. The apparatus of claim 12, wherein said means for biopsying further comprises a means for immobilizing said body part.

21. The apparatus of claim 12, further comprising a single fiducial marker used to determine the position of said Cartesian coordinates corresponding to said lesion relative to said single fiducial marker.

* * * * *